United States Patent [19]
Brock et al.

[11] Patent Number: 6,062,093
[45] Date of Patent: May 16, 2000

[54] METHOD AND APPARATUS FOR SAMPLING AGGREGATE MATERIAL

[75] Inventors: J. Donald Brock, Chattanooga, Tenn.; M. Earl Edwards, Jr., Trenton; Robert Ronald Collins, Mansfield, both of Ga.; Thomas Scott Cloninger, Chattanooga, Tenn.

[73] Assignee: Pavement Technology, Inc., Rossville, Ga.

[21] Appl. No.: 09/168,922

[22] Filed: Oct. 8, 1998

[51] Int. Cl.$^7$ .................................................... G01N 1/14
[52] U.S. Cl. ........................................................ 73/864.64
[58] Field of Search ........................... 73/864.31, 864.51, 73/864.63, 864.64, 864.67, 864.73, 864.74

[56] References Cited

U.S. PATENT DOCUMENTS

| | | | |
|---|---|---|---|
| 703,233 | 6/1902 | Brown | 73/864.64 |
| 3,459,048 | 8/1969 | Bicknell | 73/864.63 |
| 3,954,013 | 5/1976 | West | 73/864.31 |
| 4,037,476 | 7/1977 | McCrabb | 73/864.64 |
| 4,072,059 | 2/1978 | Hamilton | 73/864.64 |
| 4,616,515 | 10/1986 | Dancoine | 73/864.31 |

OTHER PUBLICATIONS

"Standard Practice for Sampling Bituminous Paving Mixtures", ASTM Designation: D 979–96, pp. 96–98, No Date.
"Standard Method of Test for Sampling Bituminous Paving Mixtures", AASHTO Designations: T 168–91, p. 321, No Date.
"GSP–15 Sampling Procedures for Asphaltic Concrete Mixtures", Georgia Department of Transportaion, Jun. 1989, pp. 1–3.
"Sampling Hot Plant Mix Material", Wyoming Department of Transportation, Mar. 1996.
Plant Sampling Procedures, Illinois Department of Transportation, pp. 4–18 and 4–21, Feb. 1998.
"Procedures for Field Testing Hot–Mix Asphalt Under MDOT's Quality Management Program: MT–77", Mississippi Department of Transportation Standard Operating Procedures, Dec. 1996.
"Standard Method of Test for Sampling Bituminous Paving Mixtures", Colorado Procedure CP–41–98, pp. 1–3, No Date.
"Sampling HMA", Indiana Test Method or Procedure No. 580–97M, Indiana Department of Transportation Materials and Tests Division, revised Nov. 24, 1997.
"Sampling Bituminous Paving Mixtures", Kentucky Method 64–425–95, No Date.
"Procedures for Sampling Stockpiled Aggregates", Indiana Test Method or Procedure No. 207–87M, Indiana Department of Transportation Materials and Tests Division, revised Feb. 14, 1996.
"Standard Practice for Sampling Aggregates", ASTM Designation: D 75–87(Reapproved 1992), pp. 16–19.

*Primary Examiner*—Robert Raevis
*Attorney, Agent, or Firm*—Chambliss, Bahner & Stophel, P.C.

[57] ABSTRACT

A sample collector for aggregate material is provided. The collector includes a collector frame having a probe that is shaped so as to be insertable along a defined axis into a quantity of aggregate material. The collector also includes a plurality of elongate support rods. The first end of each rod is attached to the probe, and a seat is provided to which the second end of each of the support rods is attached. Each rod is arranged so as to be substantially parallel to the axis, and the rods are spaced apart from each other so as to define a collection space. The collector also includes a sleeve which is adapted to slide over the collector frame between an open position which exposes the collection space and a closed position which encloses the collection space. A sliding mechanism is also provided for sliding the sleeve over the collector frame between the open position and the closed position.

10 Claims, 6 Drawing Sheets

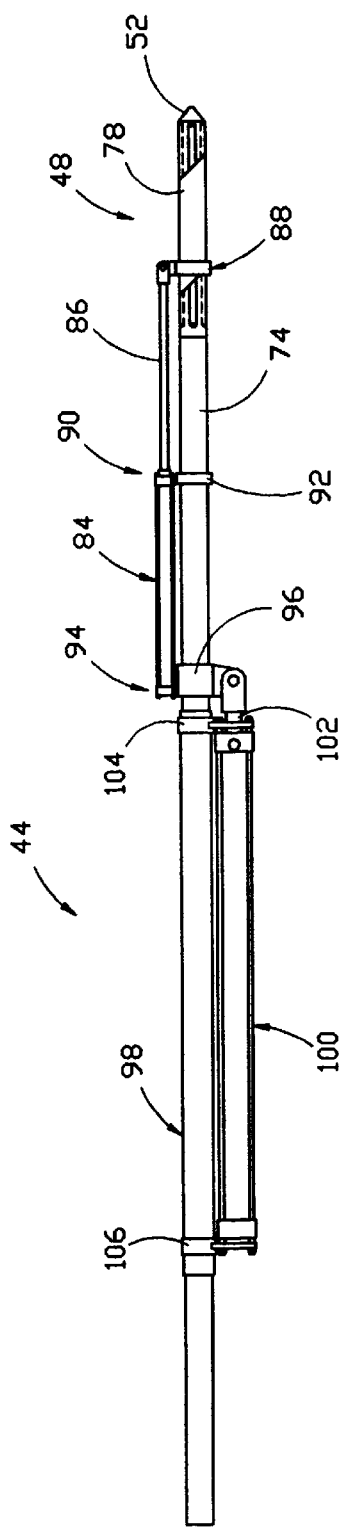
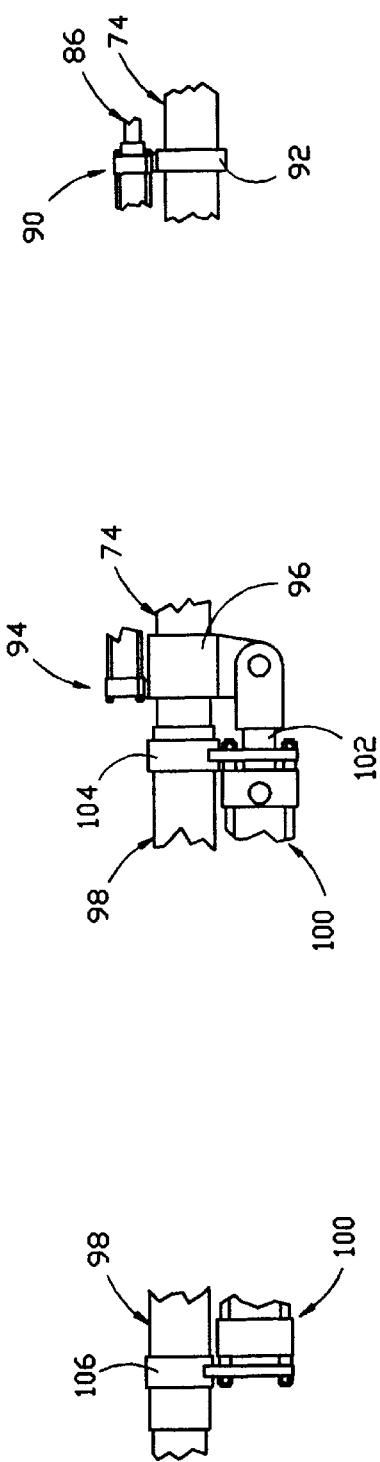
FIGURE 3
FIGURE 5
FIGURE 6
FIGURE 4

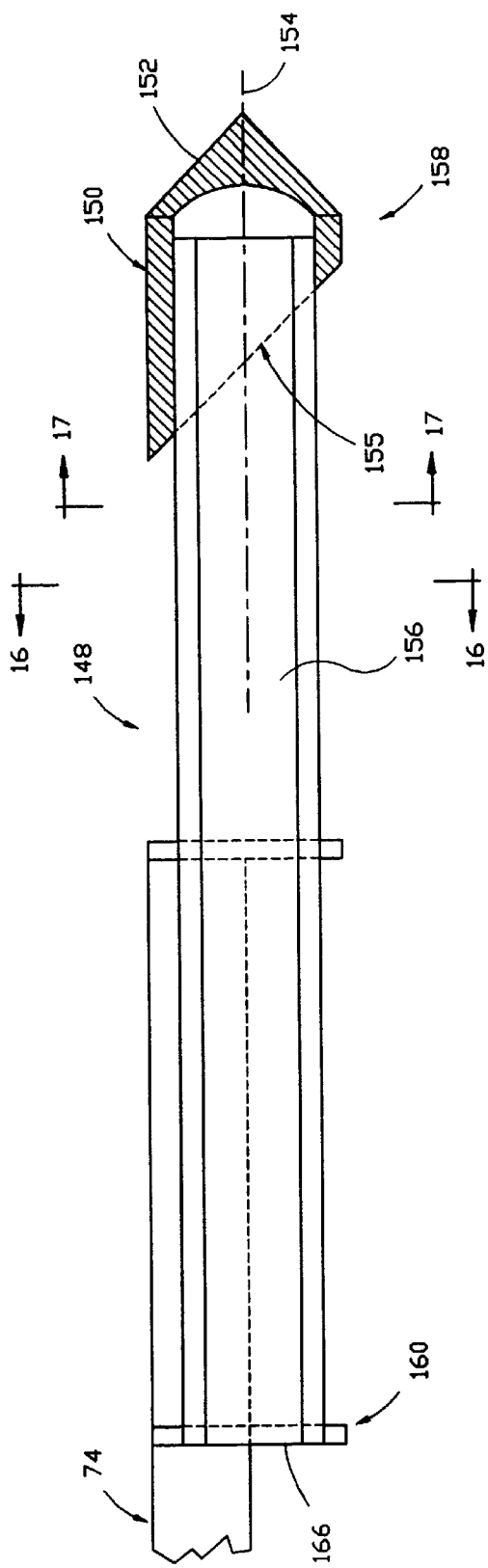
FIGURE 14
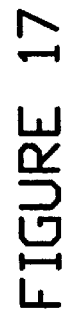
FIGURE 17
FIGURE 16
FIGURE 15

METHOD AND APPARATUS FOR SAMPLING AGGREGATE MATERIAL

FIELD OF THE INVENTION

This invention relates generally to the sampling of aggregate materials, especially to those taken from a truck, railcar, barge or other conveyance. A preferred embodiment of the invention provides a method and apparatus for the sampling of bituminous paving materials.

BACKGROUND AND DESCRIPTION OF THE PRIOR ART

Sampling of various aggregate materials is commonly required in the construction and mining industries to insure that the materials meet the required specifications for quality, composition and/or gradation. Samples of the aggregate product may be taken at various stages in the process from production or manufacture to delivery to the customer. Samples may be taken from stockpiles, silos or other storage facilities, or they may be taken from trucks, barges, railcars, conveyors or other transport vehicles.

It is common for producers of aggregate materials to sample their product at several stages, including the shipping stage. In addition, the purchaser will almost always sample at least a portion of the incoming shipments before unloading them to insure that they are acceptable. Aggregate materials that are hauled by truck are usually sampled by hand shoveling a sample portion from various locations in the aggregate load in the truck bed, in order to obtain a representative sample. Because the aggregate may segregate by size as it is being loaded and hauled, however, hand sampling in this way makes it difficult to obtain a representative sample. It is generally necessary to remove a portion of the surface material from several locations in the truck bed in order to obtain a sample portion from therebeneath. However, when the aggregate material is bituminous paving material such as asphalt concrete, its surface temperature may be as high as 250–300° F., which makes hand sampling at least uncomfortable and potentially dangerous. Furthermore, a worker who is charged with the responsibility of obtaining a hand sample from an asphalt concrete truck will not likely be willing and may not be able to spend the time to take sample portions from various locations on the load in the truck bed to insure that he gets a representative sample. Nevertheless, the standard practice for sampling bituminous paving mixtures from truck transports is to take several portions of a sample from each truck using a flat-bottom scoop or a square-nose shovel.

ASTM Designation D 979-96 specifies that at least three approximately equal increments should be taken from each truck load of bituminous paving materials sampled. Various state highway departments impose additional requirements on the sampler of asphalt concrete, in an effort to insure that representative samples are obtained. For example, the Georgia Department of Transportation Sampling Procedure GSP-15 specifies that hand samples may be taken only after the "cone" of material in the bed of the truck is first shoveled off to a depth such that the resulting flat area is at least 60% as wide as the truck and at least six inches deep. Wyoming Department of Transportation Sampling Procedure 830.0 requires that for smaller trucks, a sample area must be prepared by removing the top 2–4 inches from each quarter of the load, while for larger trucks, at least two transverse trenches must be excavated across the load in the truck bed. The sample is then removed by pushing the shovel into each cleared area or trench at a 45° angle. Illinois Department of Transportation Sampling Procedure 4.7.1 requires that an equal amount of material is to be taken from locations approximately one foot below the top of each pile in the truck bed, at quarter points around the pile's circumference. Mississippi Department of Transportation Field Testing Procedure TMD-11-77-00-000 requires that at least three samples be taken from specified locations in the truck after first removing the top 2–3 inches of material at each sample point. All of these procedures require that the sampler work for a significant period of time in the bed of the truck atop the load of hot asphalt concrete. Complying with such procedures is uncomfortable and may be dangerous, which makes proper sampling problematic.

It would be desirable therefore if a method and apparatus could be developed that would permit the taking of samples from a truck or other conveyance quickly and safely. It would also be desirable if such method and apparatus could be developed that would eliminate the need for the worker charged with obtaining the sample to climb into the truck bed and onto the load therein.

OBJECTS AND ADVANTAGES OF THE INVENTION

Accordingly, it is an object of the invention claimed herein to provide a sample collector for aggregate material that may be operated to obtain a representative sample of such material without requiring removal of the surface layer of material being sampled. It is another object of the invention to provide such a sample collector that may be operated remotely so that a worker that is charged with obtaining a sample from a truck or other means of conveyance is not required to climb onto the load of material to obtain the sample. It is yet another object of the invention to provide a method by which a mechanical sample collector may be remotely operated to obtain a representative sample of aggregate material in a safe and efficient manner.

Additional objects and advantages of this invention will become apparent from an examination of the drawings and the ensuing description.

EXPLANATION OF TECHNICAL TERMS

As used herein, aggregate materials refers to particulate materials that may be transported in bulk, including bituminous paving mixtures such as hot-mix asphalt and cold mix, crushed limestone and other types of stone, gravel, sand, lime, coal, coke, fertilizer, grain, pellets and similar materials.

As used herein, bituminous paving mixtures refers to mixtures of various aggregates, including crushed stone, sand, lime and the like, with asphalt cement or asphalt binder, which mixtures are prepared for paving purposes.

As used herein, asphalt cement or asphalt binder refers to a black or brown tar-like substance, a type of bitumen that occurs naturally or is obtained from the distillation of coal tar, wood tar or petroleum.

As used herein, asphalt concrete refers to a bituminous paving mixture that is prepared, using hot asphalt cement or asphalt binder, in a hot-mix asphalt plant. A synonymous term is hot-mix asphalt.

As used herein, cold mix refers to a bituminous paving mixture that is prepared without the use of hot asphalt cement or asphalt binder.

As used herein, elongate support rod, support rod, or rod refers to a generally straight elongate support member that may have a cross-section that is generally circular, square, rectangular, triangular, trapezoidal or of other common or convenient shape.

As used herein, sampler refers to a person who is charged with the responsibility for taking or collecting samples of aggregate material.

SUMMARY OF THE INVENTION

The invention comprises a sample collector for aggregate material, and a method for obtaining samples of aggregate material therewith. The collector has a frame which includes a probe that is shaped so as to be readily insertable along a defined axis into a quantity of aggregate material. The collector also includes a plurality of elongate support rods, each having a first end and a second end. The first end of each rod is attached to the probe, and each rod is arranged so as to be substantially parallel to the axis. The rods are spaced apart from each other so as to define a collection space, and a seat is provided, to which the second end of each of the support rods is attached. The collector also includes a sleeve that is adapted to slide over the collector frame between an open position which exposes the collection space and a closed position which encloses the collection space. The collector also includes means for sliding the sleeve over the collector frame between an open position which exposes the collection space and a closed position which encloses the collection space.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which:

FIG. 3 is a side view of a portion of the sample collector assembly of FIG. 1.

FIG. 4 is an enlarged view of a portion of the sample collector assembly of FIG. 3.

FIG. 5 is an enlarged view of a portion of the sample collector assembly of FIG. 3.

FIG. 6 is an enlarged view of a portion of the sample collector assembly of FIG. 3.

FIG. 14 is a partial sectional view of an alternative embodiment of a portion of the sample collector of the assembly of FIG. 1, with the sleeve of the collector removed to illustrate a generally open position.

FIG. 15 is a front view of the seat of the sample collector portion of FIG. 14.

FIG. 16 is a sectional view of the portion of the sample collector of FIG. 14, taken along the line 16—16 of FIG. 14.

FIG. 17 is a sectional view of the portion of the sample collector of FIG. 14, taken along the line 17—17 of FIG. 14.

DESCRIPTION OF THE PREFERRED EMBODIMENTS OF THE INVENTION

Figure 1:
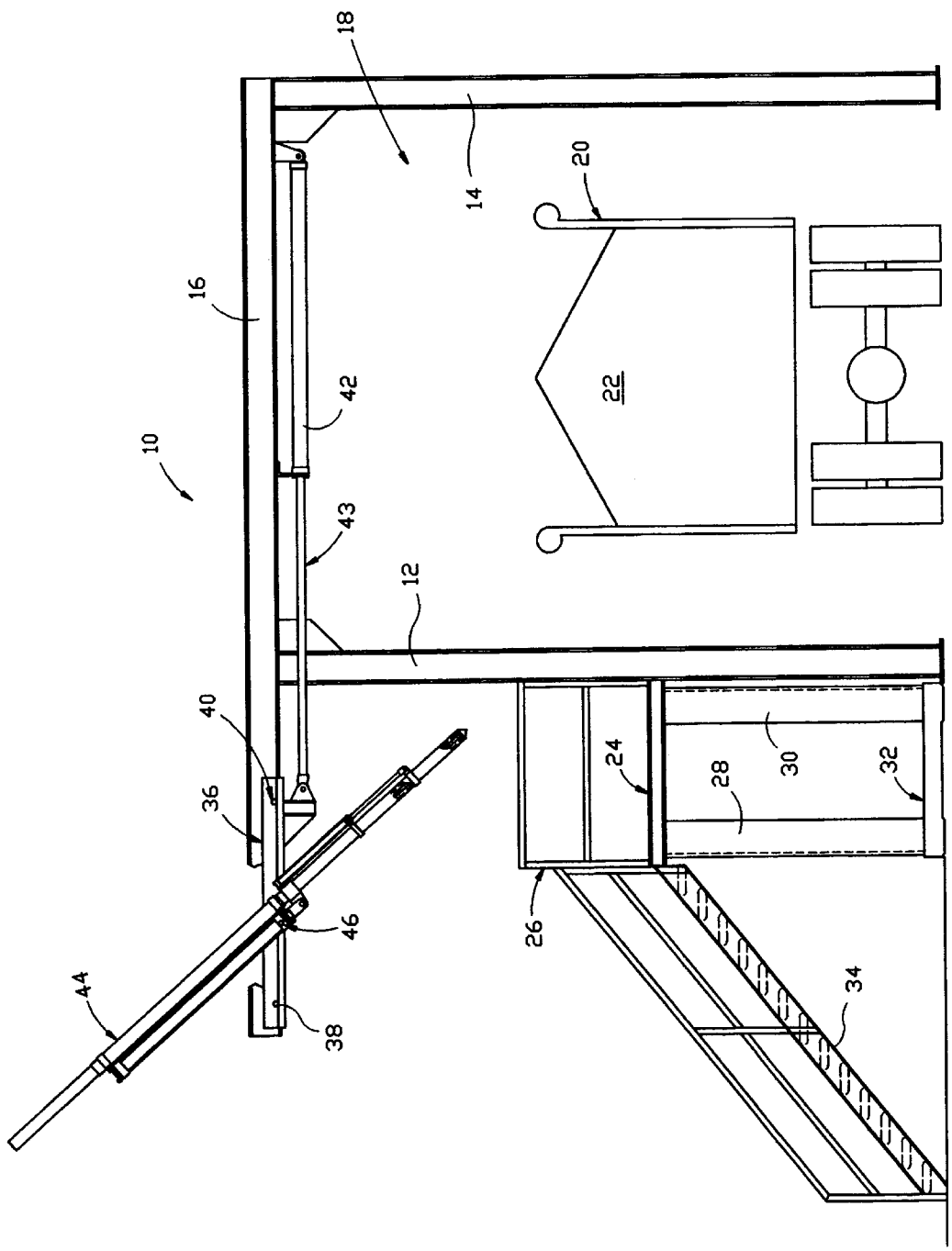
FIG. 1 is a front view of a preferred sample collector assembly that is adapted for sampling of aggregate materials from a conveyance such as a truck.
Figure 2:
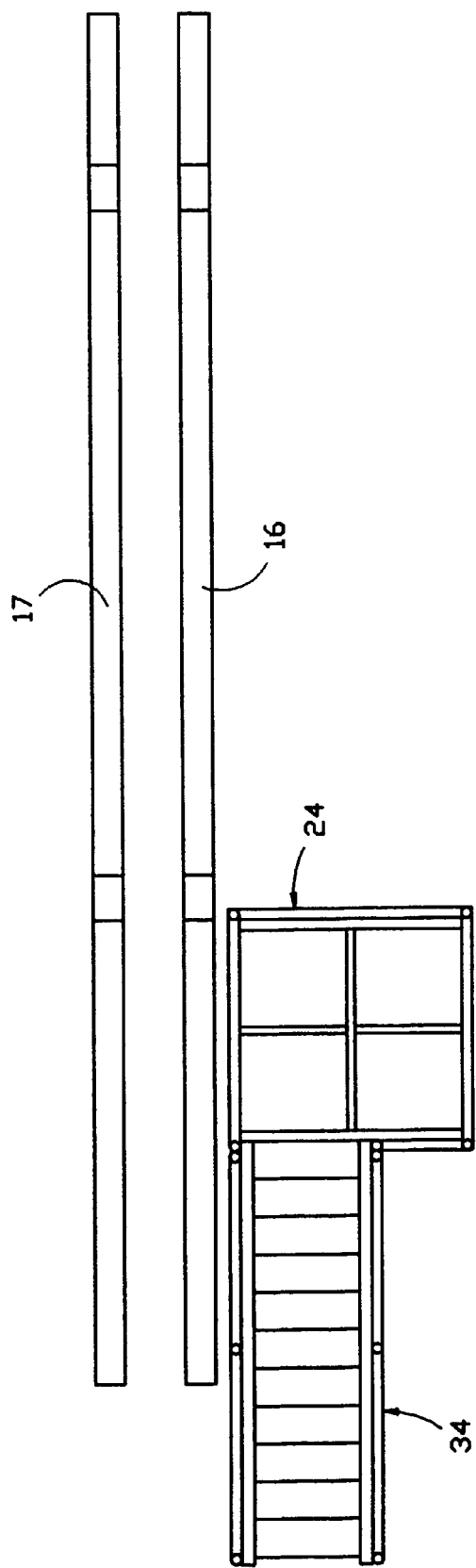
FIG. 2 is a top view of a portion of the assembly of FIG. 1.

Referring now to the drawings, FIGS. 1 and 2 illustrate a preferred embodiment of the invention, a sample collector assembly that is adapted for sampling of aggregate materials from a conveyance such as a truck. As shown therein, assembly 10 includes frame portions 12, 14, 16 and 17 (FIG. 2), preferably made of steel or other suitable material, that generally define a truck zone 18 into which truck 20, containing a load of aggregate material 22, may be driven. Of course, the frame of the assembly may be arranged in any convenient configuration, depending on whether the samples are to be taken from trucks, railcars, barges, conveyors or from stationary stockpiles.

Frame portions 16 (shown in partial cutaway in FIG. 1) and 17 define an overhead rail that is suspended over and adjacent to the truck zone. Operator's platform 24 is also located adjacent to the truck zone, and is surrounded by safety rail 26. Platform 24 is elevated by support legs, including legs 28 and 30, which are mounted on base 32. Staircase 34 provides access to the operator's platform from ground level.

Carriage 36 is adapted to ride on overhead rails 16 and 17 by means of rollers 38 and 40 between a first position adjacent to the truck zone (shown in FIG. 1) and at least one sampling position over the truck zone (not shown). Hydraulic cylinder 42 is mounted on the overhead rails and the carriage and is provided with piston 43 that is attached to the carriage so that the cylinder may move the carriage between the first position adjacent to the truck zone (shown in FIG. 1) and at least one sampling position over the truck zone. Of course, other means and mechanisms for moving the carriage between the first position and the sampling positions as are known to those skilled in the art to which the invention relates, as well as those subsequently developed, are also included within the invention.

Sample collector 44 is mounted on the carriage, preferably by pivotal connection about pivot 46. Preferably, the sample collector is adapted to pivot on the carriage so as to permit the probe to be inserted into the aggregate along an axis that is disposed at any angle within the range of about 30° to about 150° from the horizontal. In the alternative, the sample collector may be provided in the form of a portable unit that may be carried by the sampler, especially if it is used to sample stockpiled material.

FIGS. 3 through 13 illustrate a first embodiment of the sample collector in more detail. As shown therein, collector 44 includes collector frame 48, which is best shown in FIGS.

Figure 10:
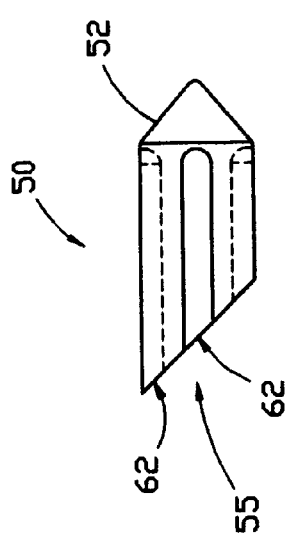
FIG. 10 is an enlarged view of a probe of the sample collector of FIG. 8.
Figure 12:
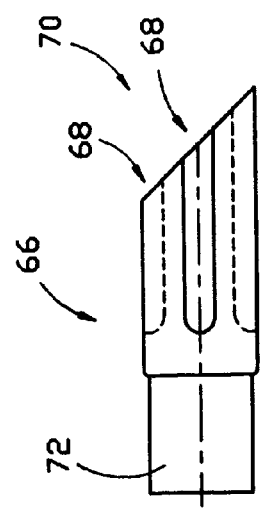
FIG. 12 is an enlarged view of a seat of the sample collector of FIG. 8.

7 and 8, and the components of which are preferably made of steel or other suitable material. Frame 48 includes probe 50 that is shaped (at first end 52) so as to be readily insertable along a defined axis, such as axis 54, into the aggregate material. Preferably, as shown in FIG. 10, probe end 52 is generally conical in shape, and rear end 55 of probe 50 forms an angle with respect to axis 54 within the range of about 30° to about 90°, or other convenient angle. Most preferably, the angle of the rear end is about 45°.

Figure 9:
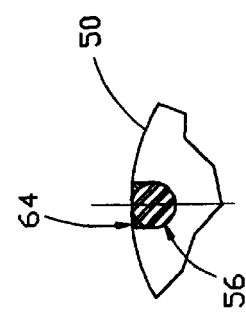
FIG. 9 is an enlarged sectional view of a portion of the sample collector of FIG. 8, taken along the line 9—9 of FIG. 8.
Figure 11:
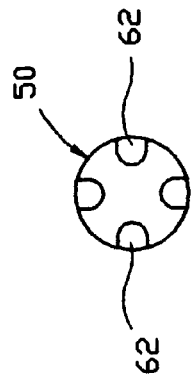
FIG. 11 is an end view of the probe of FIG. 10.
Figure 13:
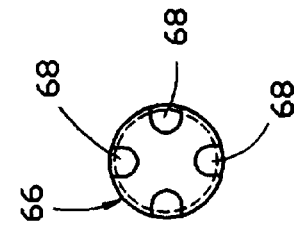
FIG. 13 is an end view of the seat of FIG. 12.

Collector frame 48 also includes a plurality of elongate support rods 56 (see FIG. 8), each having a first end 58 and a second end 60. The first end of each rod is attached to the probe, preferably by being inserted into slots 62 (FIG. 11). As shown in FIG. 9, it is also preferred that fill weld material 64 be welded around rods 56 in slots 62 and ground smooth. The second end of each of rods 56 is attached to seat 66, preferably by being inserted into slots 68. Preferably, as shown in FIG. 10, seat 66 is generally cylindrical in shape. Front end 70 of seat 66 forms an angle with respect to axis 54 within the range of about 30° to about 90°, or other convenient angle. Most preferably, the angle of the front end of seat 66 is about 45°. It is also desirable, that the angle of front end 70 of seat 66 and of rear end 55 of probe 50 be substantially the same with respect to axis 54. Rear end 72 of seat 66 is adapted to fit within extension 74 (see FIGS. 8 and 12) and is suitably attached thereto. Preferably, fill weld material (not shown) is also welded around rods 56 in slots 68 and ground smooth.

Figure 7:
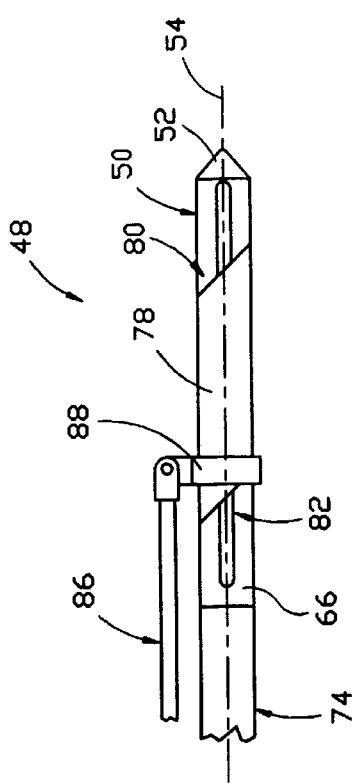
FIG. 7 is an enlarged view of a portion of the sample collector of FIG. 3, showing the sleeve of the collector in a generally closed position.
Figure 8:
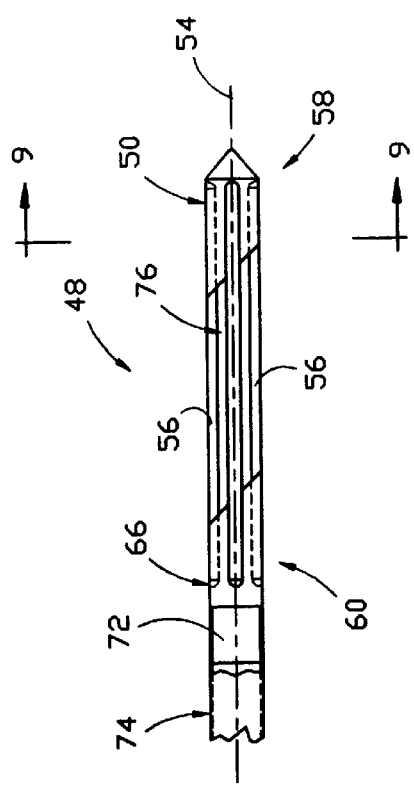
FIG. 8 is an enlarged view of a portion of the sample collector of FIG. 3, with the sleeve of the collector removed to illustrate a generally open position.

A minimum of two rods is required, although three (not shown), four (shown in FIGS. 3 through 13), or another convenient number may be employed. When the rods are provided with a generally circular cross section (such as rods 56), it is preferred that four rods be used. Each rod 56 is arranged so as to be substantially parallel to axis 54 and the rods are spaced apart from each other so as to define a collection space 76 (see FIG. 8) therebetween. Collector 44 also includes sleeve 78 which is adapted to slide over the collector frame between an open position which exposes the collection space and a closed position which encloses the collection space. Sleeve 78 is provided with an end 80 adjacent to the probe that forms an angle with respect to axis 54 within the range of about 30° to about 90°, or other convenient angle. Most preferably, this angle is 45°. As shown in FIG. 7, it is preferred that the angle of end 80 of sleeve 78 be substantially the same as the angle of rear end 55 of probe 50. Sleeve 78 is also provided with an end 82 adjacent to the seat that forms an angle with respect to axis 54 within the range of about 30° to about 90°, or other convenient angle. Most preferably, this angle is 45°. It is also preferred that the angle of end 82 of sleeve 78 be substantially the same as the angle of rear end 70 of seat 66, and that end 80 and end 82 of sleeve 78 are substantially parallel.

Hydraulic cylinder 84 (see FIG. 3) is provided for sliding the sleeve over the collector frame between an open position which exposes the collection space and a closed position which encloses the collection space. When the sleeve is in the open position, it is preferred that end 80 of sleeve 78 will be in substantial alignment with front end 70 of seat 66. Cylinder 84 is provided with piston 86 which is attached to bracket 88 (see FIGS. 3 and 7). Bracket 88 is welded, bolted or otherwise suitably attached to sleeve 78. As shown in FIGS. 3 and 6, front end 90 of cylinder 84 is supported by ring 92, which is mounted in sliding engagement with extension 74. Rear end 94 of cylinder 84 is supported by ring 96, which is attached to extension 74.

Extension 74 is mounted in sliding engagement with boom 98. Preferably, both the boom and the extension are in the shape of round or square pipes, with the extension mounted in sliding engagement within the boom and adapted to telescope therefrom. Hydraulic cylinder 100 is provided with piston 102, which is attached to ring 96, so that cylinder 100 may move extension 74 from a retracted position (shown in FIG. 3) to an extended position for inserting the collector into the aggregate material in the truck. Cylinder 100 is supported by rings 104 and 106, which are attached to boom 98. Of course, the hydraulic cylinders of the preferred embodiment of the invention that is illustrated in the drawings may be replaced by other means for moving the various components with respect to each other as are known to those having ordinary skill in the art to which the invention relates or which may be subsequently developed.

FIGS. 14 through 17 illustrate a second embodiment of the sample collector in more detail. This embodiment is of simpler construction than the embodiment of FIGS. 3 through 13, and it is more suitable for use in sampling hot-mix asphalt, as shall be subsequently explained. As shown in FIG. 14, the sample collector includes collector frame 148, the components of which are preferably made of steel or other suitable material. Frame 148 includes probe 150 that is shaped (at first end 152) so as to be readily insertable along a defined axis, such as axis 154, into the aggregate material. Preferably, probe end 152 is generally conical in shape, and rear end 155 of probe 150 forms an angle with respect to axis 154 within the range of about 30° to about 90°, or other convenient angle. Most preferably, this angle is 60°. Collector frame 148 also includes a plurality of elongate support rods 156, each having a first end 158 and a second end 160. These rods are provided with a trapezoidal or nearly trapezoidal cross-section, as shown in FIGS. 16 and 17. The first end of each rod is attached to the probe, and the second end of each of rods 156 is attached to seat 166, preferably by being welded to sides 168. Seat 166 is also preferably flat, as shown in FIG. 14, and is provided with a generally circular channel or slot 173 (shown in FIG. 15) which is adapted to receive extension 74, and to be suitably attached thereto. Preferably, intermediate support 167, similar in shape to seat 166, is also provided between seat 166 and probe 150 to further support extension 74 and to further stabilize the collector assembly.

Preferably, two rods are employed when the rods are provided with a generally trapezoidal or nearly trapezoidal cross section (such as rods 156). This will minimize sticking of hot-mix asphalt or other sticky aggregate materials to be sampled, and will facilitate cleaning of the sample collector.

Each rod 156 is arranged so as to be substantially parallel to axis 154 and to the other rod, and the rods are spaced apart from each other so as to define a collection space 176 (see FIG. 16) therebetween. The sample collector of this embodiment of the invention also includes a sleeve (not shown), similar to sleeve 78, which is adapted to slide over the collector frame between an open position which exposes the collection space and a closed position which encloses the collection space. Preferably, the sleeve is provided with a front end adjacent to the probe that forms an angle with respect to axis 154 within the range of about 30° to about 90°, or other convenient angle. It is also preferred that the angle of the front end of the sleeve be substantially the same as the angle of rear end 155 of probe 150. It is also preferred that the sleeve be provided with a rear end (away from the probe) that forms a 90° angle with respect to axis 154 so that the sleeve will align with intermediate support 167 when the sleeve is in the open position.

In the practice of the illustrated embodiments of the invention, truck 20 is driven into truck zone 18. Carriage 36 with the sample collector pivotally mounted thereon is moved by the action of cylinder 42 from the first position adjacent to the truck zone to a sampling position over the truck zone. The sample collector is then pivoted to the desired angle, and cylinder 84 is actuated (if necessary) to slide the sleeve (such as sleeve 78 of FIGS. 3 and 7) over the collector frame to a closed position. Extension 74 is then moved with respect to boom 98 by the action of cylinder 100 from a retracted position to an extended position so as to insert the collector into the aggregate material in the truck. Preferably, the collector is inserted so that the probe is imbedded to a depth of at least about twelve inches in the material in the truck.

Cylinder 84 is then actuated to slide sleeve 78 over the collector frame to an open position which exposes the collection space (such as space 76 defined by rods 56). This will allow a sample of the aggregate to fall into or otherwise fill the collection space. Cylinder 84 is again actuated to slide the sleeve over the collector frame to a closed position which encloses the collection space and contains the sample of the aggregate material therein. An alternative sequence may be employed, depending primarily on the type of aggregate material being sampled, in which the collector may be inserted into the aggregate material with the sleeve in the open position which exposes the collection space. Then cylinder 84 may be actuated to slide the sleeve over the collector frame to a closed position which encloses the collection space and contains a sample of the aggregate material therein.

Cylinder 100 is then actuated to move extension 74 from the extended position to a retracted position to withdraw the collector from the aggregate material in the truck. Cylinder 42 may then be actuated to move the carriage to the first position adjacent to the truck zone, and cylinder 84 may again be actuated to slide the sleeve over the collector frame to an open position which exposes the collection space and allows the sample to be withdrawn therefrom. Additional samples may then be taken, if desired, from other locations in the truck bed, by changing the angle and/or the location at which the probe is inserted into the aggregate, as well as by moving the truck within the truck zone, if desired.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations, and the same are intended to be comprehended within the meaning and range of equivalents of the appended claims.

What is claimed is:

1. A sample collector assembly for use in sampling aggregate material from a truck having an open bed, said assembly comprising:
    (A) an assembly frame which includes an overhead rail that is suspended over and adjacent to a truck zone into which the truck has been driven;
    (B) a carriage which is adapted to ride on the overhead rail between a first position adjacent to the truck zone and at least one sampling position over the truck zone;
    (C) means for moving the carriage between the first position and at least one sampling position over the truck zone;
    (D) a sample collector which is attached to the carriage and which comprises:
        (i) a collector frame which includes:
            (a) a probe that is shaped so as to be insertable along a defined axis into the aggregate material;
            (b) a plurality of elongate support rods, each having a first end and a second end, wherein the first end of each rod is attached to the probe, and wherein each rod is arranged so as to be substantially parallel to the axis, and wherein the rods are spaced apart from each other so as to define a collection space;
            (c) a seat to which the second end of each of the support rods is attached;
        (ii) a sleeve which is adapted to slide over the collector frame between an open position which exposes the collection space and a closed position which encloses the collection space;
        (iii) means for sliding the sleeve over the collector frame between an open position which exposes the collection space and a closed position which encloses the collection space;
        (iv) an elongate extension which is attached to the seat;
        (v) a boom to which the elongate extension is mounted in sliding engagement therewith;
        (vi) means for moving the elongate extension from a retracted position to an extended position for inserting the collector into the aggregate material in the truck.

2. The sample collector assembly of claim 1 wherein the carriage-moving means comprises a hydraulic cylinder.

3. The sample collector assembly of claim 1 wherein the sleeve-sliding means comprises a hydraulic cylinder.

4. The sample collector assembly of claim 1 wherein the means for moving the extension with respect to the boom comprises a hydraulic cylinder.

5. The sample collector assembly of claim 1 wherein the sleeve is provided with an end adjacent to the probe that forms an angle with respect to the axis within the range of about 30° to about 90°.

6. The sample collector assembly of claim 5 wherein the sleeve is provided with an end adjacent to the probe that forms an angle with respect to the axis of approximately 45°.

7. The sample collector assembly of claim 5 wherein the sleeve is provided with an end adjacent to the probe that forms an angle with respect to the axis of approximately 60°.

8. The sample collector assembly of claim 1 wherein the sample collector is pivotally attached to the carriage.

9. The sample collector assembly of claim 8 wherein the sample collector is adapted to pivot on the carriage so as to permit the probe to be inserted into the aggregate along an axis that is disposed at an angle within the range of about 30° to about 150° from the horizontal.

10. A method for sampling aggregate material from the open bed of a truck, comprising:
    (A) providing an assembly frame which includes an overhead rail that is suspended over and adjacent to a truck zone into which the truck has been driven;
    (B) providing a carriage which is adapted to ride on the overhead rail between a first position adjacent to the truck zone and at least one sampling position over the truck zone;
    (C) providing means for moving the carriage between the first position and at least one sampling position over the truck zone;
    (D) providing a sample collector which is attached to the carriage and which comprises:

(i) a collector frame which includes:
  (a) a probe that is shaped so as to be insertable along a defined axis into the aggregate material;
  (b) a plurality of elongate support rods, each having a first end and a second end, wherein the first end of each rod is attached to the probe, and wherein each rod is arranged so as to be substantially parallel to the axis, and wherein the rods are spaced apart from each other so as to define a collection space;
  (c) a seat to which the second end of each of the support rods is attached;
(ii) a sleeve which is adapted to slide over the collector frame between an open position which exposes the collection space and a closed position which encloses the collection space;
(iii) means for sliding the sleeve over the collector frame between an open position which exposes the collection space and a closed position which encloses the collection space;
(iv) an elongate extension which is attached to the seat;
(v) a boom to which the elongate extension is mounted in sliding engagement therewith;
(vi) means for moving the elongate extension from a retracted position to an extended position for inserting the collector into the aggregate material in the truck;

(E) moving the carriage from the first position to a sampling position over the truck zone;

(F) moving the elongate extension from a retracted position to an extended position so as to insert the collector into the aggregate material in the truck;

(G) sliding the sleeve over the collector frame to an open position which exposes the collection space;

(H) sliding the sleeve over the collector frame to a closed position which encloses the collection space and contains a sample of the aggregate material therein;

(I) moving the elongate extension from the extended position to a retracted position to withdraw the collector from the aggregate material in the truck;

(J) moving the carriage to the first position adjacent to the truck zone;

(K) sliding the sleeve over the collector frame to an open position which exposes the collection space and allows the sample to be withdrawn therefrom.

* * * * *